(12) United States Patent
Moureaux et al.

(10) Patent No.: US 11,838,530 B2
(45) Date of Patent: Dec. 5, 2023

(54) METHOD FOR CONCEALING DATA IN AN IMAGE OR A VIDEO STREAM INSIDE A COMPRESSION CHAIN

(71) Applicants: UNIVERSITE DE LORRAINE, Nancy (FR); UNIVERSITE DE STRASBOURG, Strasbourg (FR)

(72) Inventors: Jean-Marie Moureaux, Saint-Max (FR); Amine Chaabouni, Nancy (FR); Yann Gaudeau, Niederhausbergen (FR)

(73) Assignees: UNIVERSITE DE LORRAINE, Nancy (FR); UNIVERSITE DE STRASBOURG, Strasbourg (FR)

( * ) Notice: Subject to any disclaimer, the term of this patent is extended or adjusted under 35 U.S.C. 154(b) by 136 days.

(21) Appl. No.: 17/310,685

(22) PCT Filed: Feb. 20, 2020

(86) PCT No.: PCT/EP2020/054566
§ 371 (c)(1),
(2) Date: Aug. 17, 2021

(87) PCT Pub. No.: WO2020/169781
PCT Pub. Date: Aug. 27, 2020

(65) Prior Publication Data
US 2022/0078464 A1 Mar. 10, 2022

(30) Foreign Application Priority Data

Feb. 21, 2019 (FR) ........................ 1901743

(51) Int. Cl.
*H04N 19/467* (2014.01)
*H04N 19/124* (2014.01)
(Continued)

(52) U.S. Cl.
CPC ......... *H04N 19/467* (2014.11); *H04N 19/124* (2014.11); *H04N 19/176* (2014.11);
(Continued)

(58) Field of Classification Search
CPC .. H04N 19/467; H04N 19/124; H04N 19/176; H04N 19/18; H04N 19/593;
(Continued)

(56) References Cited

U.S. PATENT DOCUMENTS 6,621,933 B2 9/2003 Chung et al.
7,006,631 B1 2/2006 Luttrell et al.
(Continued)

OTHER PUBLICATIONS

Liu, Y., et al..; "Reversible Data Hiding Scheme Based on H.264/ AVC without Distortion Drift," Journal of Software, vol. 7, No. 5, May 2012, pp. 1059-1065. (Year: 2012).*
(Continued)

*Primary Examiner* — Dramos Kalapodas
(74) *Attorney, Agent, or Firm* — Greer, Burns & Crain, Ltd (57) ABSTRACT

A method for concealing data in an image or a video stream inside a compression chain, being implemented by a computer and including a structuring and processing phase, during which at least one image is structured into blocks including coefficients, a phase of converting and quantifying blocks so as to generate converted and quantified coefficients, with entropic coding intended to code the converted and quantified coefficients. The method includes a step of concealing data, during which bits of the data are concealed by modifying converted and quantified coefficients located in a high frequency zone of at least some of the blocks that relate to the luminance component of the video stream and that are intra-coded. This modification is performed after the quantification but before the entropic coding.

13 Claims, 3 Drawing Sheets

(51) Int. Cl.
| | |
|---|---|
| *H04N 19/176* | (2014.01) |
| *H04N 19/18* | (2014.01) |
| *H04N 19/593* | (2014.01) |
| *H04N 19/625* | (2014.01) |
| *H04N 19/63* | (2014.01) |
| *H04N 19/91* | (2014.01) |
| *G16H 30/40* | (2018.01) |
| *G16H 80/00* | (2018.01) |

(52) U.S. Cl.
CPC .......... *H04N 19/18* (2014.11); *H04N 19/593* (2014.11); *H04N 19/625* (2014.11); *H04N 19/63* (2014.11); *H04N 19/91* (2014.11); *G16H 30/40* (2018.01); *G16H 80/00* (2018.01)

(58) Field of Classification Search
CPC ...... H04N 19/625; H04N 19/63; H04N 19/91; H04N 19/11; H04N 19/159; H04N 19/48; G16H 30/40; G16H 80/00; G06T 2201/0052; G06T 2201/0053; G06T 1/0035
See application file for complete search history.

(56) References Cited

U.S. PATENT DOCUMENTS

| | | | |
|---|---|---|---|
| 7,720,305 B2* | 5/2010 | Shi | ............... H04N 1/32154 |
| | | | 382/275 |
| 2022/0417515 A1* | 12/2022 | Chen | ............... H04N 19/129 |

OTHER PUBLICATIONS

International Search Report and Written Opinion received for PCT/EP2020/054566, dated Apr. 22, 2020.
French Search Report received for Application No. 1901743, dated Nov. 22, 2019.
Cao, L., et al., "Perception-driven Watermarking with Evolutionary Block Mapping," Visual Communications and Image Processing, Proc. of SPIE, vol. 7744, 2010, 8 pages.
Lin, Y., "High capacity reversible data hiding scheme based upon discrete cosine transformation," The Journal of Systems and Software 85, 2012, pp. 2395-2404.
Liu, Y., et al., "Reversible Data Hiding Scheme Based on H.264/AVC without Distortion Drift," Journal of Software, vol. 7, No. 5, May 2012, pp. 1059-1065.

* cited by examiner

Vertical

Horizontal

Diagonal

METHOD FOR CONCEALING DATA IN AN IMAGE OR A VIDEO STREAM INSIDE A COMPRESSION CHAIN

BACKGROUND

The present invention relates to a method for concealing data in an image or a video stream inside a compression chain.

A particularly beneficial application of the invention is in the field of ENT medical videos and telemedicine, but it has a wider scope, as it can be applied to any field in which a compression chain is used with the deployment of blocks such as described below.

Data concealment, also known as "data hiding", is a technique that makes it possible to hide an item of information, in the form of a mark or a message, in a digital document. Different types of information can be hidden, such as text, a signature, a code, an image, a video or audio.

This recent technique was initially designed in the 1990s in the fight against software piracy and to protect intellectual property in identical copies, particularly following significant expansion in the use of digital media during transmission and storage over very open data networks that are vulnerable to intentional and/or unintentional attacks.

Today, new challenges have been brought to the fore through different research studies and applications.

In fact, in addition to its use for copyright and authentication, data hiding can also be employed for the transportation of metadata, for error correction or reducing information redundancy, of use for improving the performance of coding systems.

Since its creation, data concealment has been developed in several fields such as for example telecommunications, encoding of images/videos, video on demand (VOD) services, medical imaging and computer security.

Data hiding techniques can be classified in several different categories:
- covert channel: this is a communication channel, established between two computers, which uses the bandwidth of another channel in an invisible manner in order to transmit data without the knowledge of the network administrator. This concept is very sensitive in the context of network security.
- steganography: this is the concealment of one or more messages in another message such that it is invisible without the ability to detect it. It is different from cryptography, which is intended above all to protect a message by rendering it incomprehensible by not permitted persons to use it, for reasons of security such as protecting data confidentiality, authenticity and integrity. Steganography can be used with text by hiding the message in letters (linguistic steganography) or in a phrase, or in a media support (technical steganography) such as audio or image. It was widely used during the second world war.
- anonymization: this consists of preventing mention of the name or publishing of the private data of a person out of respect for their private life.
- copyright marking: this is concealment of the information in a document in order to protect copyright. With respect to the state of the art in steganography, copyright techniques can be visible or invisible. In this context, watermarking and fingerprinting are the two best-known techniques based on this concept of data concealment.

For each application, the principal constraints to be complied with are: capacity, imperceptibility/invisibility and robustness.

There are different data concealment methods in image and video using different characteristics. For example information can be concealed according to:
- insertion domain: spatial, frequency (or spectral), multi-resolution or content-based.
- mode of insertion of the mark: additive scheme, substitution scheme.

In the prior art, it is known to carry out concealment within the compression chain.

The document by Y. Liu, Z. Li and X. Ma, "Reversible Data Hiding Scheme Based On H.264/AVC without Distortion Drift", Journal of Software, vol. 7, April 2012 is known, describing a technique for concealing bits directly in the transformation and quantization module.

U.S. Pat. No. 6,621,933B2 is known, which describes a watermarking method utilizing the MPEG2 compression standard. Watermarking is carried out within the compression chain between transformation and quantization.

U.S. Pat. No. 7,006,631B1 is known, which describes a method for concealing a watermark by modifying the codes of the entropy encoder. Concealment is therefore directly implemented within the entropy encoder.

The aim of the present invention is a new method making it possible to conceal a maximum of data while preserving visual quality.

Another object of the invention is to solve the problem of low throughput in networks with limited capacity.

SUMMARY

At least one of the aforementioned objectives is achieved with a method for concealing data in an image or a video stream inside a compression chain, this method being implemented by computer and comprising the following steps:
- a phase of structuring and processing during which at least one image is structured in blocks containing coefficients,
- a phase of transformation and quantization of the blocks so as to generate transformed and quantized coefficients;
- an entropy encoding intended to encode the transformed and quantized coefficients, characterized in that it also comprises a data concealment step during which bits from said data are concealed by modifying transformed and quantized coefficients, situated in a zone of high frequencies of at least a part of said blocks which are relative to the luminance component of the video stream and are intra-coded;
and in that this modification is carried out after the quantization but before the entropy encoding.

The invention can be applied to an image or to a video stream. By "block" is meant a block as defined in the HEVC standard (also known as H.265) or a macroblock as defined in the AVC standard (also known as H.264) or any block generated by a transform of the DCT type, for example.

With the method according to the invention, the data are concealed in real time inside the compression chain. Application of these data on all or part of the blocks allows a compromise to be chosen between the quality of the image and the quantity of concealed data. This allows intelligent rendering of the video or image according to the needs of the user.

The invention consists of an original method making it possible to hide as much information as possible in a video, while retaining acceptable visual quality. To this end, a zonal approach was used for concealment of the data in frequencies to which the human eye has little sensitivity, while optimizing the compression time. This is extremely beneficial in certain applications such as for example transmission over a low-throughput sensor network. It is possible for example to transfer an electrocardiogram signal in real time without increasing the transmission rate or deploy telemedicine throughout regions equipped with low-throughput connections. This contributes to the fight against medical deserts.

The method according to the invention thus makes it possible at the same time to compress and conceal different types of multimedia data in a media support of the image or video type. The data can be concealed during compression, during live transmission and/or video storage, without increasing the data size/transfer cost.

Advantageously, the zone of high frequencies can be situated under the lower right diagonal of a square matrix of a block.

The transform can be a discrete cosine transform (DCT), discrete sine transform (DST), or discrete wavelet transform (DWT) using blocks of the transform unit (TU) type.

Generally, following a transform, such as the discrete cosine transform (DCT) or discrete sine transform (DST) used in the latest compression standards such as H.264 and HEVC, the information is distributed in two different frequency zones: the upper left part, above the diagonal of a DCT block (the low frequencies) and the lower right part, below the diagonal (the mid and high frequencies).

As the human eye is more sensitive to the low frequencies than the high, the important information of the image is essentially expressed by the transformed coefficients of the upper zone. Thus the invention has a clever approach, concealing the data in the high frequencies, which makes it possible to limit the visual impact of the image quality degradation due to the insertion of data.

This zonal approach makes it possible to reach significant capacities ranging up to 3 Mb for example for an ENT endoscope sequence of only 10 s compressed to 5 Mb/s with the HEVC standard.

Advantageously, the data can be concealed in a video stream, these data constituting a concealed stream.

The method according to the invention makes it possible for example to conceal a medical stream in another stream during a tele-transmission session. This makes it possible to reduce the number of medical streams to be sent on a given platform.

Thus it is possible to meet the low-throughput constraints encountered in particular in networks in the medical sector. Inasmuch as the transmission of different streams remotely in real time requires a significant bandwidth, the fact of hiding one stream in another makes it possible to reduce the number of streams exchanged between the different sites during a remote consultation session for example.

According to a feature of the invention, the concealed data can constitute a watermark. This is a concealed object for an application for the protection of copyright or confidential data.

According to an advantageous embodiment of the invention, data concealment is only carried out on TU blocks of predetermined size. It is possible for example to limit the concealment solely to TU blocks of size 4×4, or 8×8, or 16×16 or preferably, 32×32, depending on the nature of the images/videos processed.

According to the invention, the modification algorithm can comprise the following steps:

if the bit to be concealed is equal to 1, the transformed and quantized coefficient must be non-zero; if the transformed and quantized coefficient is zero before concealment, it is modified to 1, otherwise it retains its value, if the bit to be concealed is equal to 0, the transformed and quantized coefficient must be zero if it was different to 0 before concealment.

Despite the addition of the operations due to this data concealment algorithm, it has been shown that the processing time used by the machine during compression drops slightly with respect to compression without concealment. This drop can be explained by the increase in the number of "0s" after cancelling the significant values, following application of the insertion algorithm. The greater the number of insignificant (zero) transformed quantized coefficients, the lighter the processing load on the encoder during compression. This result confirms the simplicity and efficiency of the algorithm according to the invention.

Thus, the method according to the invention does not increase the consumption of CPU resources, regardless of the quantity of information inserted. This is compatible with operation in real time.

According to an advantageous feature of the invention, for a predefined concealment level k, k being comprised between 1 and N−1 for a TU block of size N×N, the modification applies only to the coefficients aligned on a row parallel to the diagonal, this row being the $k^{th}$ row from this diagonal.

In other words, in a TU block, it is possible to choose to apply the concealment on only a part of coefficients located under the diagonal so as to limit distortion of the image.

According to another advantageous feature of the invention, the method can comprise a step of applying a visual prominence to the processed image, the modification being carried out on the most prominent TU blocks or on the least prominent TU blocks.

Visual prominence is a technique that makes it possible to define the prominent objects in an image, the zone on which the eyes concentrate during viewing of a video, i.e. the objects having characteristics perceived as important by the visual system. This prominent zone, having an item of relevant information spatially located in the image, can be useful for determining the regions of interest (ROI) in an image.

Depending on the type of video stream processed, it can be advantageous to conceal the data only in the TU blocks of the prominent parts of the image. This is the case for example in ENT endoscope videos where the region of interest is limited. But it may however be advantageous to conceal the data only in the TU blocks of the non-prominent parts of the image. This is the case for example in videos where the information of interest is distributed throughout the image.

According to the invention, the most prominent blocks can be those having a prominence value greater than or equal to a predetermined threshold comprised between 0 and 1.

To this end, it is possible to generate a file giving a prominence coefficient for each TU block. Subsequently, it is easy to apply a prominence threshold equal to 0.4 for example (between 0 and 1). A TU block is then called prominent if the average of all its transformed quantized coefficients is greater than 0.4. In this case it is assigned a value equal to 1. Otherwise, it is assigned a 0.

According to another aspect of the invention, a data encoder is proposed, configured to implement the method described above. By way of example, this encoder can be configured to implement the H.264 or H.265 standard. Specifically, the data can be concealed according to the invention after a DCT/DST transform and a quantization, but before a CABAC entropy encoding.

The invention also relates to a data decoder configured to extract the data concealed according to the method of the invention.

The data can be extracted while the video is read and can be combined so as to constitute another video stream.

A computer program product is also proposed, comprising instructions which, when the program is executed by a computer, control the latter to implement the steps of the method according to the invention.

BRIEF DESCRIPTION OF THE DRAWINGS

Other advantages and features of the invention will become apparent on examination of the detailed description of an embodiment that is in no way limitative, and from the attached drawings, in which.

DETAILED DESCRIPTION

The embodiments that will be described hereinafter are in no way limitative, in particular, variants of the invention can be implemented comprising only a selection of the features described hereinafter, in isolation from the other features described, if this selection of features is sufficient to confer a technical advantage or to differentiate the invention with respect to the state of the prior art. This selection comprises at least one, preferably functional, feature without structural details, or with only a part of the structural details if this part alone is sufficient to confer a technical advantage or to differentiate the invention with respect to the state of the prior art.

In particular, all the variants and all the embodiments described are intended to be combined together in any combinations where there is no objection thereto from a technical point of view.

The different embodiments of the present invention comprise various steps. These steps can be implemented by machine instructions executable by means of a microprocessor for example.

Alternatively, these steps can be carried out by specific integrated circuits comprising a wired logic for executing the steps, or by any combination of programmable components and customized components.

The present invention can also be provided in the form of a computer program product that can comprise a non-transient computerized memory media containing instructions executable on a computerized machine, these instructions being capable of being used to program a computer (or any other electronic device) for executing the method.

Figure 1:
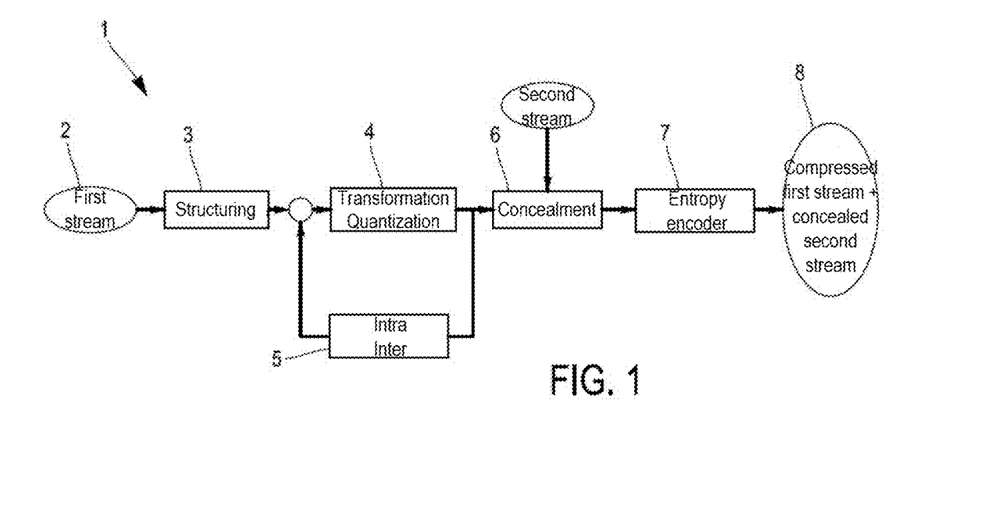
FIG. 1 is a simplified diagrammatic view of a compression chain or encoder according to the invention.

FIG. 1 shows an overall view of a compression chain 1 receiving a video sequence 2 as input. This chain operates in a closed loop inasmuch as the data already coded are available for processing the current part. Reference is made to causal data that is obtained via a decoding loop integrated in the chain. The input video is processed sequentially, image by image, each image being divided into slices representing all or part of an image. The slices are themselves divided into blocks in standard H.265 or macroblocks of size 16×16 pixels in standard H.264, the macroblocks being able to be partitioned into rectangles of smaller sizes. The blocks or macroblocks are processed according to a "raster" route, starting at the top left of the image and finishing at the bottom right.

According to the standard H.265, each image undergoes data structuring in module 3; this allows a separation between different blocks (coding tree units or CTU), with sizes 16×16, 32×32 or 64×64. Each CTU can be divided into smaller blocks, called coding units (CU). Thus a coding partition tree is defined, called a quadtree. In fact, starting from root, each node can be divided recursively into four square coding blocks (CB) having the same size. This difference makes it possible to have higher calculation performance. Thus, a homogeneous zone in an image can have blocks of size 64×64 and the heterogeneous regions or the parts of the video with a high degree of movement can be divided into smaller blocks, 4×4 for example, so as to enhance the details of the video.

Other partition tree structures are embedded on the leaves of the coding quadtree. These subdivisions are associated with the prediction and the residual, called "quadtree residual", before applying the frequency transform and the quantization of the residual coefficients.

Thus, each CU block can be composed of several PUs (prediction units) and TUs (transform units) depending on the type of prediction (intra or inter), and the level of the quadtree. These units are responsible for the decision mode of the prediction and application of the transform in each CU block.

One luminance block and two chrominance blocks correspond to each CU block.

The TU blocks then undergo a DCT transform and a quantization within the module 4. The loop 5 contains in particular a prediction step making it possible to reduce considerably the quantity of information to be transmitted, improving the compression level correspondingly. There are two types of pixel prediction, intra and inter, according to whether spatial or temporal redundancies are utilized respectively. Intra prediction is similar to fixed image coding and utilizes the causal data within the current image, and more particularly neighbouring images, of the current set of pixels. Inter prediction carries out movement compensation based on a previously encoded image on which a movement estimation has been made. The nature of the blocks processed in the transformation and quantization module can thus be intra or inter. The present invention specifically targets intra blocks, in particular intra luminance blocks.

The loop 5 therefore samples the residuals exiting the transformation and quantization module 4 and reinjects the result as input to this transformation and quantization module 4 via a comparator receiving the structured images.

Thus, each of the blocks undergoes the prediction steps generating a residual of pixels based on the causal data, transformation and quantization of the residual. The residuals exiting the module 4 are coefficients placed in the TU blocks. According to the invention, the intra-coded TU blocks of the luminance component will undergo data concealment processing in module 6. These data can be a digital marker stored in memory or a second video stream. The TU blocks then contain the transformed and quantized coefficients, concealing data according to the invention. These TU blocks then power an entropy encoder 7 of the CABAC (context-adaptive binary arithmetic coding) type, directly or via a shaping module (not shown). The output is a compressed stream 8 including the second stream, the bits of which are concealed according to the invention. The entropy encoder generally also receives signalling information necessary for decoding the stream. The binary stream obtained at the output of the encoder can then be read by a decoder that restores a video by repeating the steps in inverse fashion.

FIG. 1 makes it possible to visualize clearly at which site the concealment function according to the invention is carried out, which distinguishes the invention from a large part of the techniques of the prior art.

Figure 2:
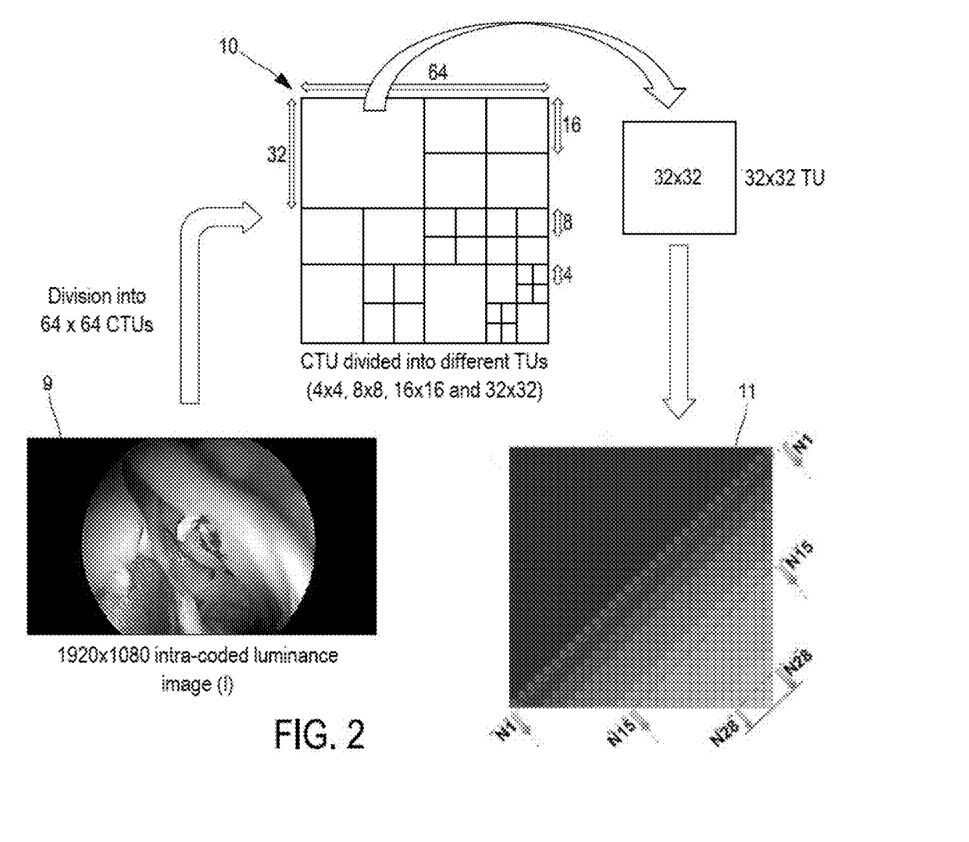
FIG. 2 is a diagrammatic view illustrating the method according to the invention.

FIG. 2 shows in further detail the concealment method according to the invention. An image 9 can be seen that is an intra-coded luminance image with a resolution of 1920×1080.

Structuring makes it possible to obtain a CTU block 10 of size 64×64. This block is divided into different TU blocks of sizes 4×4, 8×8, 16×16 and 32×32. According to an example embodiment of the invention, the 32×32 TU block on which the data concealment according to the invention will be applied is selected alone or in addition to other blocks. Data concealment is carried out in the transformed quantized coefficients by the zonal approach from level N1 to level N31 as can be seen in block 11 in FIG. 2.

A level 1 concealment can be defined, making it possible to hide the data in the thirty one rows of coefficients, parallel to the diagonal and situated in the lower right corner: from N1 to N31. It is also possible to define another level 15 making it possible to modify the seventeen rows from N15 to N31.

Figure 3:
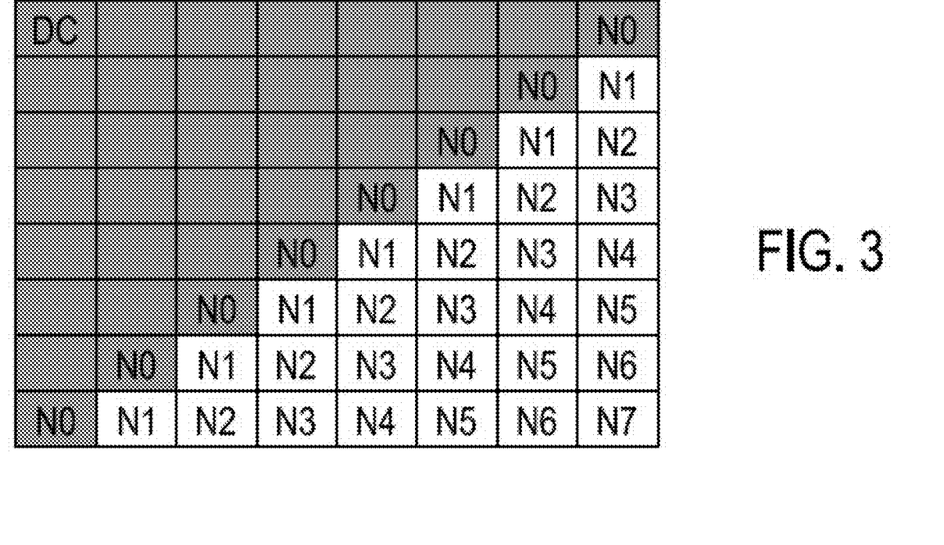
FIG. 3 is a diagrammatic view of an 8×8 TU block comprising seven levels of transformed and quantized coefficients numbered from one to seven.

FIG. 3 shows an 8×8 TU block illustrating the seven levels of transformed and quantized coefficients numbered from 1 to 7. In this example, for an 8×8 block (N=8), it is possible to define seven (N−1) levels with respect to the diagonal, in which it is possible to modify the transformed and quantized coefficients. The coefficients relating to the low frequencies are not shown. The diagonal is shown diagrammatically with the reference N0. The high-frequency coefficients are shown diagrammatically with references Ni, i ranging from 1 to 7. For reasons of simplicity and to identify the rows parallel to the diagonal, coefficients of the same row carry the same reference Ni.

For a selected level k, it is possible to conceal the message in all the coefficients of the levels N−k shown. Thus, at each level, it is possible to modify a percentage of coefficients in the TU block. As shown in Table 3.1, concealing information at level 2 for an 8×8 TU block corresponds to modifying approximately 33% of the coefficients of this block.

TABLE 1

| Level | % Coefficients to be modified |
|---|---|
| 1 | 43.75 |
| 2 | 32.81 |
| 3 | 23.44 |
| 4 | 15.63 |
| 5 | 9.38 |
| 6 | 4.69 |
| 7 | 1.56 |

The second table indicates the percentage of coefficients to be modified to conceal information in the case of a 32×32 TU block.

TABLE 2

| Level | % Coefficients to be modified |
|---|---|
| 1 | 48.44 |
| 2 | 45.41 |
| 3 | 42.48 |
| 4 | 39.65 |
| 5 | 36.91 |
| 6 | 34.28 |
| 7 | 31.74 |
| 8 | 29.30 |
| 9 | 26.95 |
| 10 | 24.71 |
| 11 | 22.56 |
| 12 | 20.51 |
| 13 | 18.55 |
| 14 | 16.70 |
| 15 | 14.94 |
| 16 | 13.28 |
| 17 | 11.72 |
| 18 | 10.25 |
| 19 | 8.89 |
| 20 | 7.62 |
| 21 | 6.45 |
| 22 | 5.37 |
| 23 | 4.39 |
| 24 | 3.52 |
| 25 | 2.73 |
| 26 | 2.05 |
| 27 | 1.46 |
| 28 | 0.98 |
| 29 | 0.59 |
| 30 | 0.29 |
| 31 | 0.10 |

In order to further improve the efficiency of the method, provision is made in particular cases to apply visual prominence on medical videos so as to select only a part of the TU blocks.

Visual prominence makes it possible to define the prominent objects in an image, zones considered to display elements of interest. It is then possible to choose to apply concealment only on the blocks forming part of the prominent zones, or blocks forming part of zones that are not prominent.

Prominence is expressed by a value ranging from 0 to 1.

Figure 5:
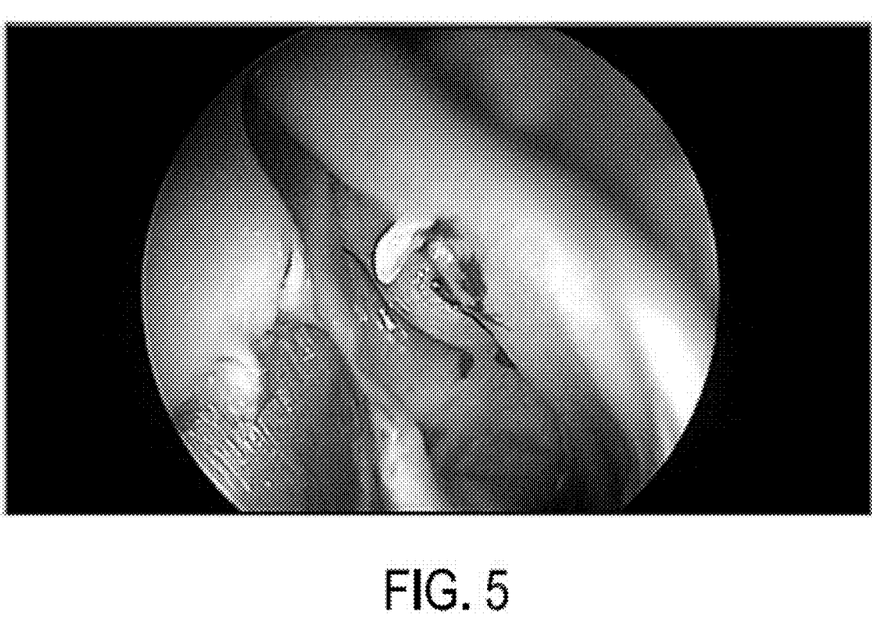
FIG. 5 is a view illustrating an endoscope video sequence.

For example, for certain medical images of the ENT type, such as the image in FIG. 5, the useful zone is the central part. Thus, by applying the prominence technique, the inner circular part, which represents the medical information, is more prominent that the outer part all in black.

The prominent zones (inner circular part) contain more significant coefficients than the zones that are not prominent (black part).

It is possible to generate a file giving a prominence coefficient for each TU block. For example, if a prominence threshold equal to 0.4 (between 0 and 1) is set, a TU block is then called prominent if the average of all its transformed quantized coefficients is greater than 0.4. In this case it is assigned a value equal to 1. Otherwise, it is assigned a 0.

Based on this file, only the prominent blocks can be used to conceal the data. Such an implementation makes it possible to improve the capacity and quality of the concealment.

But it can be appropriate to retain only blocks that are not prominent, for example for very busy images. The significant coefficients are located over the entire image and not in one specific part or zone.

With the present invention, it is therefore possible to select all or part of the intra-coded TU blocks of the luminance component. The selected blocks then undergo concealment processing consisting of modifying all or part of the high-frequency coefficients of these blocks.

Advantageously, this concealment processing is implemented by means of a concealment algorithm according to the invention so as to insert a large quantity of data in a simple manner. This algorithm can be the following:

TABLE 3

| Input | Transformed and quantized coefficient C(i,j) of the luminance component/Concealed bit Tb |
|---|---|
| Output | Coefficient after concealment $C_r(i,j)$ |
| 1 | START |
| 2 | If Tb = 1 then |
| 3 | If C(i,j) = 0 then |
| 4 | $C_r(i,j) = 1$ |
| 5 | Else $C_r(i,j) = C(i,j)$ |
| 6 | End |
| 7 | Else (If Tb = 0) |
| 8 | $C_r(i,j) = 0$ |
| 9 | End |
| 10 | END |

If the bit to be concealed Tb is equal to 1, the transformed and quantized coefficient C(i,j) must be non-zero. If it is zero before concealment, it is modified to 1, if not, it retains its value. This manipulation minimizes the distortion that could occur after the concealment.

Otherwise (Tb=0) the algorithm cancels the coefficient C(i,j) if it was different to 0 before concealment.

This algorithm can for example be integrated in a real-time ×265 encoder.

Figure 4:
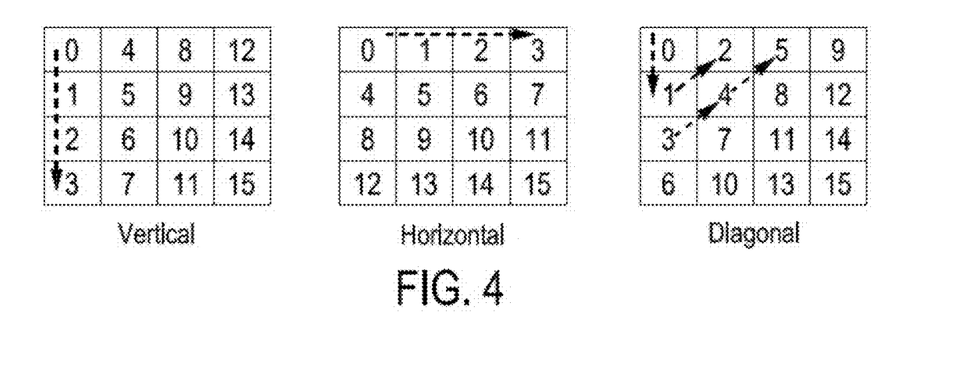
FIG. 4 is a diagrammatic view of three modes of reading 4×4 TU blocks.

Before hiding the data, the read mode of the coefficients for each TU block must be determined so as to take account thereof during the concealment. This read mode depends on the size of the block and the prediction mode applied for generating the coefficients. Three read modes are defined in the HEVC standard:

Vertical reading: TU size 4×4 and 8×8 for the intra predictions {6, 7, 8, 9, 10, 12, 13, 14}

Horizontal reading: TU size 4×4 and 8×8 for the intra predictions {22, 23, 24, 25, 26, 27, 28, 29, 30}

Diagonal reading: TU size 4×4 and 8×8 for the intra predictions {0, 1, 2, 3, 4, 5, 15, 16, 17, 18, 19, 20, 21, 31, 32, 33, 34, 35} and TU size 16×16 and TU size 32×32 for all the intra predictions.

These three read modes are shown in FIG. 4 in the example of a 4×4 TU block.

Knowledge of the read mode is advantageous for the functioning of the algorithm at the time of insertion and extraction of the concealed message. This makes it possible to verify if the coefficient being analysed is in fact in the selected zone before applying the concealment. This verification is carried out by the position and order of each coefficient in the associated TU block. For example, a coefficient 12 in an 8×8 block in vertical read mode is not equal to the coefficient 12 in an 8×8 block that follows the horizontal read mode. The same principle applies for each coefficient except the first coefficient and last coefficient of the block.

Following the same steps as those for insertion, the algorithm for extraction of the message can be the following:

TABLE 4

| Input | Coefficient after concealment $C_r(i,j)$ |
|---|---|
| Output | Concealed bit Tb |
| 1 | START |

TABLE 4-continued

| 2 | If $C_r(i,j)$ = 0 then |
|---|---|
| 3 | Tb = 0 |
| 4 | Else (If $C_r(i,j)$ < > 0) |
| 5 | Tb = 1 |
| 6 | End |
| 7 | END |

Thus, the modified coefficient $C_r(i,j)$ is zero, the concealed bit Tb is zero. Otherwise, it is equal to 1. This algorithm makes it possible to simplify the processing at the decoder, which must not take significant additional processing time during decoding of the video.

For example, for medical video sequences, with an associated read mode for a ×265 compression, at a rate of 5 Mb/s with a standard configuration of five intra-coded images I for 10 s, the results are displayed in the two following tables. Table 5 shows the distribution of TU blocks according to the read mode. Table 6 shows the distribution of TU blocks according to their size.

TABLE 5

| Reading mode of TU block | Sequence 2 (%) |
|---|---|
| Diagonal | 99.9 |
| Horizontal | 0.1 |
| Vertical | 0 |

TABLE 6

| Size of TU block | Sequence 2 (%) |
|---|---|
| 4 × 4 | 0.1 |
| 8 × 8 | 0.4 |
| 16 × 16 | 4.4 |
| 32 × 32 | 95.1 |

These results show that the majority of the TU blocks are of large size 32×32 (95.1%) and with diagonal reading (99.9%) for this type of medical video.

To simplify the method according to the invention, the concealment can be applied only to the 32×32 blocks with diagonal reading mode.

Furthermore, it has been noted that despite the addition of the operations due to the algorithm according to the invention, the processing time used during compression drops slightly with respect to compression without concealment. This drop can be explained by the increase in the number of "0s" after cancelling the significant values, following application of the method according to the invention. The greater the number of insignificant (zero) transformed quantized coefficients, the lighter the processing load on the encoder during compression. This result confirms the simplicity and efficiency of the concealment method according to the invention. Thus, this method does not increase the consumption of CPU resources, regardless of the quantity of information inserted, this being an advantageous parameter for real-time applications.

The present invention is a new approach to data concealment, allowing the transport of additional metadata for a constant cost. To this end, the data are inserted into TU blocks after quantization and before CABAC entropy encoding, more precisely in the lower right zone with respect to the diagonal of the intra-coded TU blocks associated with the luminance component. This zonal approach makes it possible to reach significant capacities ranging up to 3 Mb for an ENT endoscope sequence of only 10 s.

Furthermore, it is possible to define different insertion levels, which renders the technique capable of parametrization and development, thus making it possible to manage capacity as a function of quality.

The visual prominence technique makes it possible to reduce the number of blocks to be processed, while still improving the capacity (quantity of blocks concealed) and the quality (visual appearance).

Of course, the invention is not limited to the examples that have just been described, and numerous modifications may be made to these examples without exceeding the scope of the invention.

The invention claimed is:

1. A method for concealing data in an image or a video stream inside a compression chain, this method being implemented by computer and comprising the following steps:
   a phase of structuring and processing during which at least one image is structured in blocks containing coefficients;
   a phase of transformation and quantization of the blocks so as to generate transformed and quantized coefficients;
   an entropy encoding intended to encode the transformed and quantized coefficients;
   a data concealment step during which bits from the data are concealed by modifying transformed and quantized coefficients, situated in a zone of high frequencies of at least a part of said blocks which are relative to the luminance component of the video stream and which are intra-coded,
   in that this modification is carried out after the quantization but before the entropy encoding;
   and for a predefined concealment level k, k being comprised between 1 and N−1 for a block of size N×N, the modification applies only to the coefficients aligned below a diagonal concealment level taken across the N×N block.

2. The method according to claim 1, characterized in that data concealment is only carried out on blocks of predetermined size.

3. The method according to claim 1, characterized in that the modification comprises the following steps:
   if the bit to be concealed is equal to 1, the transformed and quantized coefficient must be non-zero; if the transformed and quantized coefficient is zero before concealment, it is modified to 1, otherwise it retains its value,
   if the bit to be concealed is equal to 0, the transformed and quantized coefficient is equal to 0.

4. The method according to claim 1, characterized in that the zone of high-frequencies is the zone situated under the lower right part, below a square matrix of a block.

5. The method according to claim 1, characterized in that it comprises a step of applying a visual prominence to the processed image, the modification being carried out on the most prominent blocks or on the least prominent blocks.

6. The method according to claim 5, characterized in that the most prominent blocks are those having a prominence value greater than or equal to a predetermined threshold comprised between 0 and 1.

7. The method according to claim 1, characterized in that the data are concealed in a video stream, these data constituting a concealed stream.

8. The method according to claim 1, characterized in that the concealed data constitute a watermark.

9. The method according to claim 1, characterized in that the transform is a discrete cosine transform (DCT), discrete sine transform (DST), or discrete wavelet transform (DWT) using blocks of the transform unit (TU) type.

10. A data encoder configured to implement the method according to claim 1.

11. The encoder according to claim 10, characterized in that it is configured to implement the H.264 or H.265 standard.

12. A data decoder configured to extract the data concealed according to the method of claim 1.

13. A computer code program stored in a non-transient computerized memory media, comprising instructions which, when the program is executed by a computer, control the latter to implement the steps of the method according to claim 1.

* * * * *